(12) United States Patent
Hattori et al.

(10) Patent No.: US 10,627,393 B2
(45) Date of Patent: Apr. 21, 2020

(54) LATEX AGGLUTINATION INHIBITION IMMUNOASSAY

(71) Applicant: SEKISUI MEDICAL CO., LTD., Tokyo (JP)

(72) Inventors: Keiko Hattori, Tokyo (JP); Souichi Kitano, Tokyo (JP); Michiko Kawamoto, Tokyo (JP)

(73) Assignee: SEKISUI MEDICAL CO., LTD., Tokyo (JP)

(*) Notice: Subject to any disclaimer, the term of this patent is extended or adjusted under 35 U.S.C. 154(b) by 105 days.

(21) Appl. No.: 14/418,824

(22) PCT Filed: Jul. 31, 2013

(86) PCT No.: PCT/JP2013/070775
§ 371 (c)(1),
(2) Date: Mar. 13, 2015

(87) PCT Pub. No.: WO2014/021387
PCT Pub. Date: Feb. 6, 2014

(65) Prior Publication Data
US 2015/0212075 A1    Jul. 30, 2015

(30) Foreign Application Priority Data

Jul. 31, 2012   (JP) ................................. 2012-170603

(51) Int. Cl.
*G01N 33/53*     (2006.01)
*G01N 33/543*    (2006.01)
*C08L 71/02*     (2006.01)

(52) U.S. Cl.
CPC .......... *G01N 33/5306* (2013.01); *C08L 71/02* (2013.01); *G01N 33/54313* (2013.01); *G01N 33/54393* (2013.01); *C08G 2650/58* (2013.01); *C08L 2203/02* (2013.01); *G01N 2400/00* (2013.01)

(58) Field of Classification Search
CPC ...................................................... G01N 33/53
See application file for complete search history.

(56) References Cited

U.S. PATENT DOCUMENTS

| | | | | |
|---|---|---|---|---|
| 4,060,597 A * | 11/1977 | Sato | ................. | G01N 33/54313 422/69 |
| 5,136,095 A * | 8/1992 | Tarnowski | ....... | G01N 33/54313 564/286 |
| 5,164,321 A | 11/1992 | Zdunek et al. | | |
| 5,612,459 A * | 3/1997 | Toma | ................. | C07K 16/1292 424/184.1 |
| 5,627,080 A | 5/1997 | Cheng et al. | | |
| 2005/0118163 A1 * | 6/2005 | Mizushima | .......... | A61K 9/0019 424/130.1 |
| 2007/0054873 A1 * | 3/2007 | MacLachlan | ........ | A61K 31/573 514/44 R |
| 2009/0238437 A1 * | 9/2009 | Levine | ................... | G01N 33/49 382/134 |
| 2011/0318765 A1 * | 12/2011 | Miyazaki et al. | ........... | 435/7.93 |

FOREIGN PATENT DOCUMENTS

| | | |
|---|---|---|
| EP | 0 221 282 A2 | 5/1987 |
| EP | 2439533 A1 | 4/2012 |
| GB | 1384399 A | 2/1975 |
| JP | 62-71860 A | 4/1987 |
| JP | 62-071860 A | 4/1987 |
| JP | 64-44855 A | 2/1989 |
| JP | 6-300761 A | 10/1994 |
| JP | 10-506184 A | 6/1998 |
| JP | 2002-502979 A | 1/2002 |
| JP | 2007-121204 A | 5/2007 |
| JP | 2008-157931 A | 7/2008 |
| JP | 2011-038903 A | 2/2011 |
| JP | 2011-38903 A | 2/2011 |
| JP | 2012-78161 A | 4/2012 |
| JP | 2012-078161 A | 4/2012 |
| WO | WO 99/40442 A1 | 8/1999 |

OTHER PUBLICATIONS

Wikipedia (https://en.wikipedia.org/wiki/Hexadimethrine_bromide, print retrieved on Oct. 24, 2016).*
Corti et al. "A Receptor-Antibody Sandwich Assay for Teicoplanin", Clin. Chem., vol. 33, No. 9, pp. 1615-1618, published 1987.*
Chemical Book (Hexadimethrine Bromide <http://www.chemicalbook.com/ChemicalProductProperty_DE_cb1327317.htm>, print retrieved on Jan. 6, 2016).*
Guidechem.com (Noigen DS 601 <http://www.guidechem.com/dictionary/en/9005-08-7.html>, print retrieved on Nov. 26, 2017).*
English translation of International Preliminary Report on Patentability dated Feb. 12, 2015, in PCT International Application No. PCT/JP2013/070775.
Extended European Search Report dated Nov. 30, 2015, for European Application No. 13825736.5.

(Continued)

*Primary Examiner* — Tracy Vivlemore
*Assistant Examiner* — Nam P Nguyen
(74) *Attorney, Agent, or Firm* — Birch, Stewart, Kolasch & Birch, LLP (57) ABSTRACT

A problem of the present invention is to provide a method capable of avoiding nonspecific reactions which result in the absence of agglutination that should occur in agglutination inhibition LTIA. The present invention provides a method of avoiding nonspecific reactions in a latex agglutination inhibition test by performing a latex agglutination inhibition assay in the presence of one or more compounds selected from the group consisting of polyoxyethylene-polyoxypropylene block copolymers, polyoxyethylene alkyl ethers, polyoxyethylene fatty acid esters, and polyvalent quaternary amine polymer compounds.

15 Claims, 3 Drawing Sheets

(56) References Cited

OTHER PUBLICATIONS

International Search Report issued in PCT/JP2013/070775, dated Oct. 22, 2013.
International Search Report dated Oct. 22, 2013, in PCT International Application No. PCT/JP2013/070775.

* cited by examiner

LATEX AGGLUTINATION INHIBITION IMMUNOASSAY

TECHNICAL FIELD

The present invention relates to a method of avoiding nonspecific reactions caused by some kind of component in a blood sample in a latex turbidimetric immunoassay and a reagent used in the method.

BACKGROUND ART

A latex turbidimetric immunoassay (hereinafter also referred to as LTIA) is a method of measuring a test substance (analyte) by using latex particles to which antigens or antibodies are immobilized (antigen- or antibody-immobilized latex particles), and is widely used in the field of clinical examination. Methods of measuring an antigen which is an analyte (analyte antigen) by LTIA are roughly classified into a method of forming a sandwich type immune complex through a reaction between an anti-analyte antibody-immobilized latex particle and an analyte antigen so as to measure the analyte (antigen) from the level of agglutination of the latex particles associated with the formation of an immune complex (hereinafter also referred to as sandwich LTIA), and a method of causing an antigen-immobilized latex particle and an antigen (analyte) in a test sample to compete with each other so that the formation of an immune complex is inhibited between the latex particle and the antibody so as to measure the analyte (antigen) from the level of agglutination inhibition of the latex particles associated with the inhibition of formation of the immune complex (hereinafter also referred to as agglutination inhibition LTIA).

In LTIA, it is commonplace that an agglutination of antigen- or antibody-immobilized latex particles that should not occur does occur due to some kind of component in a test sample even through an analyte is not present in the test sample such as serum, conversely, it is also common that an agglutination that should occur does not occur. This is referred to as a nonspecific reaction and is known to cause various measurement errors.

A known method for avoiding nonspecific reactions is a technique in which various substances are added to a reaction system.

Patent Document 1 describes a method in which an inorganic boron compound is added to a sample solution in combination with a buffer system as a method for removing a nonspecific turbidity (synonymous with nonspecific agglutination) in the sandwich LTIA. However, this method is a method of removing the occurrence of agglutination that should not occur in an assay using antibody-immobilized latex particles and is not a method capable of dealing with the absence of agglutination that should occur in agglutination inhibition LTIA.

In the case of measurement of a blood sample by agglutination inhibition LTIA, even if the blood sample does not contain an analyte, only a lower degree of agglutination is in some cases acquired than the degree of agglutination acquired when measurement is performed by using as a test sample a buffer solution containing no blood component, due to an effect of some kind of component in the blood sample. Alternatively, the degree of agglutination (absorbance) is in some cases not identical and different between the cases of diluting, with a buffer solution and with a buffer solution containing a blood component, a standard substance for concentration calibration of an analyte in a test sample (hereinafter also referred to as a concentration calibration-standard substance). However, as described above, no method has been established for avoiding nonspecific reactions which disrupt the agglutination that should occur in agglutination inhibition LTIA even in the present time and a new method needs to be developed.

CITATION LIST

Patent Literature

Patent Document 1: Japanese Laid-Open Patent Publication No. 64-044855

SUMMARY OF INVENTION

Technical Problem

An object of the present invention is to provide a method capable of avoiding nonspecific reactions which disrupt the agglutination that should occur in agglutination inhibition LTIA.

Solution to Problem

As a result of intensive studies for solving the problem in agglutination inhibition LTIA, the present inventors have found that, by preliminarily adding into a buffer solution for diluting a concentration calibration-standard substance one or more compound(s) for avoiding nonspecific reactions (nonspecific reaction-avoidance compound(s)) selected from the group consisting of polyoxyethylene-polyoxypropylene block copolymers (hereinafter also referred to as POE-POP block copolymers), polyoxyethylene alkyl ethers (hereinafter also referred to as POE alkyl ethers), polyoxyethylene fatty acid esters (hereinafter also referred to as POE fatty acid esters), and polyvalent quaternary amine polymer compounds, the difference can be reduced between the degree of agglutination acquired by measurement on the buffer solution itself as a test sample and the degree of agglutination acquired by measurement on a blood sample containing no analyte, thereby completing the present invention.

The present invention has the following configuration.

<1> A method of avoiding nonspecific reactions in a latex agglutination inhibition test, comprising performing a latex agglutination inhibition assay in the presence of one or more compounds selected from the group consisting of polyoxyethylene-polyoxypropylene block copolymers, polyoxyethylene alkyl ethers, polyoxyethylene fatty acid esters, and polyvalent quaternary amine polymer compounds.

<2> The method of <1>, wherein the nonspecific reactions are nonspecific reactions which disrupt the agglutination that should occur when an analyte is not present in a test sample.

<3> The method of <1> or <2>, wherein the polyoxyethylene-polyoxypropylene block copolymers are represented by Formula (I):

$$HO(C_2H_4O)_a\text{---}(C_3H_6O)_b\text{---}(C_2H_4O)_cH \qquad (I)$$

(wherein a, b, and c denote arbitrary integers and a+c is determined so as to represent an ethylene oxide with an average degree of polymerization of 4 to 200 units while b is determined so as to represent a propylene oxide with an average degree of polymerization of 5 to 100 units).

<4> The method of <1> or <2>, wherein the polyoxyethylene alkyl ethers are represented by Formula (II):

$$R^1O(C_2H_4O)_nH \quad (II)$$

(wherein $R^1$ denotes an alkyl group having a carbon number of 8 to 20 (the alkyl group may be either primary or secondary and may have one or more double bonds in the alkyl group) and n denotes an arbitrary integer from 7 to 40).

<5> The method of <1> or <2>, wherein the polyoxyethylene fatty acid esters are represented by Formula (III):

$$R^2COO(C_2H_4O)_nR^3 \quad (III)$$

(wherein $R^2$ denotes an alkyl group having a carbon number of 16 to 18 (the alkyl group may have one or more double bonds) and n denotes an arbitrary integer from 170 to 180 while $R^3$ denotes a hydrogen atom or an $R^2COO$ group).

<6> The method of <1> or <2>, wherein the polyvalent quaternary amine polymer compounds are polybrene (CAS number: CB1327317).

<7> A reagent for a latex agglutination inhibition test, wherein one or more compounds selected from the group consisting of polyoxyethylene-polyoxypropylene block copolymers, polyoxyethylene alkyl ethers, polyoxyethylene fatty acid esters, and polyvalent quaternary amine polymer compounds are contained in any one or more of following (1) to (4):

(1) a concentration calibration-standard substance,
(2) a solution containing an anti-analyte antibody,
(3) a solution containing antigen-immobilized latex particles, and
(4) a solution for dissolving or diluting the concentration calibration-standard substance.

<8> The reagent of <7> for use in the measurement of teicoplanin in a human blood sample.

<9> An agent for avoiding nonspecific reactions for use in a latex agglutination inhibition test comprising as an active ingredient one or more compounds selected from the group consisting of polyoxyethylene-polyoxypropylene block copolymers, polyoxyethylene alkyl ethers, polyoxyethylene fatty acid esters, and polyvalent quaternary amine polymer compounds.

Advantageous Effects of Invention

The present invention provides a method of avoiding nonspecific reactions which disrupt the agglutination that should occur in agglutination inhibition LTIA. The present invention enables accurate measurement of an analyte in a blood sample by agglutination inhibition LTIA.

DESCRIPTION OF EMBODIMENTS (Nonspecific Reaction-Avoidance Compound)

A nonspecific reaction-avoidance compound of the present invention may be one or more compounds selected from the group consisting of POE-POP block copolymers, POE alkyl ethers, POE fatty acid esters, and polyvalent quaternary amine polymer compounds.

The polyoxyethylene-polyoxypropylene block copolymers (POE-POP block copolymer) of the present invention have a structure represented by following Formula (I):
[Chem 1]

$$HO(C_2H_4O)_a\text{—}(C_3H_6O)_b\text{—}(C_2H_4O)_cH \quad (I)$$

(wherein a, b, and c denote arbitrary integers and a+c is determined so as to represent an ethylene oxide (hereinafter also referred to as EO) with an average degree of polymerization of 4 to 200 units while b is determined so as to represent a propylene oxide (hereinafter referred to as PO) with an average degree of polymerization of 5 to 100 units).

Specific examples of commercial products containing the POE-POP block copolymers used in the present invention can be products categorized into "F" out of nonionic surfactants generally marketed under the name of "Pluronic (registered trademark)", or nonionic surfactants marketed under the name of "Epan (registered trademark)".

The POE-POP block copolymers are described as an ingredient in several types of indication of ingredients and identity or similarity can be confirmed among indication of ingredients; however, numerical values may not completely match among indication of ingredients even for the commercial products with the same name. This is characteristic of polymers and is obviously understood by those skilled in the art.

More specific examples of the commercial products are listed along with confirmable indication of ingredients, (1) and (2).

Pluronic F77:
(1) polyoxyethylene content is 70%, polyoxypropylene molecular weight is about 2306
(2) EO number-PO number: (52×2)-35

Pluronic F87:
(1) polyoxyethylene content is 70%, polyoxypropylene molecular weight is about 2644
(2) EO number-PO number: (62×2)-39

Pluronic F88:
(1) polyoxyethylene content is 80%, polyoxypropylene molecular weight is about 2644
(2) EO number-PO number: (97×2)-39

Pluronic F68:
(1) polyoxyethylene content is 80%, polyoxypropylene molecular weight is about 1967
(2) EO number-PO number: (75×2)-30

Epan 485:
(1) polyoxyethylene content is 85%, polyoxypropylene molecular weight is about 1200
(2) EO number-PO number: (80×2)-21

Epan 680:
(1) polyoxyethylene content is 80%, polyoxypropylene molecular weight is about 1750
(2) EO number-PO number: (84×2)-30

Epan 785:
(1) polyoxyethylene content is 85%, polyoxypropylene molecular weight is about 2000
(2) EO number-PO number: (140×2)-34
Epan 750:
(1) polyoxyethylene content is 50%, polyoxypropylene molecular weight is about 2000
(2) EO number-PO number: (23×2)-34

Among these products, Pluronic F88 and Pluronic F68 are listed also in Japanese Standards of Quasi-drug Ingredients 2006.

The polyoxyethylene alkyl ethers (POE alkyl ethers) of the present invention have a structure represented by following Formula (II):

[Chem 2]

$$R^1O(C_2H_4O)_nH \quad (II)$$

(wherein $R^1$ denotes an alkyl group having a carbon number of 8 to 20 (the alkyl group may be either primary or secondary and may have one or more double bonds in the alkyl group) and n denotes an arbitrary integer from 7 to 40).

Specific examples of commercial products containing the POE alkyl ethers used in the present invention can be products categorized into "BT", "BC", or "BO" out of nonionic surfactants generally marketed under the name of "NIKKOL (registered trademark)".

More specific examples of the commercial products will be listed along with confirmable indication of ingredients, (3) and (4).
NIKKOL BC40TX:
(3) polyoxyethylene cetyl ether
(4) $R^1$: carbon number 16, n: 40
NIKKOL BO10TX:
(3) polyoxyethylene oleyl ether
(4) $R^1$: carbon number 18, n: 10
NIKKOL BT-7:
(3) polyoxyethylene alkyl ether
(4) $R^1$: carbon number 12 to 14 (secondary alkyl), n: 7
NIKKOL BT-9:
(3) polyoxyethylene alkyl ether
(4) $R^1$: carbon number 12 to 14 (secondary alkyl), n: 9.

The polyoxyethylene fatty acid esters (POE fatty acid esters) of the present invention have a structure represented by following Formula (III):

$$R^2COO(C_2H_4O)_nR^3 \quad (III)$$

(wherein $R^2$ denotes an alkyl group having a carbon number of 16 to 18 (the alkyl group may have a double bond(s)) and n denotes an arbitrary integer from 170 to 180 while $R^3$ denotes a hydrogen atom or an $R^2COO$ group).

Specific examples of commercial products containing the POE fatty acid esters used in the present invention can be products categorized into "DS" out of nonionic surfactants generally marketed under the name of "Noigen (registered trademark)".

More specific examples of the commercial products will be listed along with confirmable indication of ingredients, (5) and (6):
Noigen DS-601.
(5) polyoxyethylene distearic acid ester
(6) $R^1$: carbon number 17, n: 175

The polyvalent quaternary amine polymer compounds may be polybrene (CAS number: CB1327317).

Among these products, Pluronic F88, NIKKOL BT-7, and NIKKOL BT-9 are preferred.

The nonspecific reaction-avoidance compound of the present invention can be used by adding to one or more reagents for performing agglutination inhibition LTIA such as a concentration calibration-standard substance (so-called calibrator), a solution containing an anti-analyte antibody, a solution containing antigen-immobilized latex particles, and a solution for dissolving or diluting the concentration calibration-standard substance. The nonspecific reaction-avoidance compound is particularly preferably added to the concentration calibration-standard substance.

A preferable concentration of the nonspecific reaction-avoidance compound is 0.003 to 0.078% (v/v, the same applies to the following), more preferably 0.006 to 0.034%, and particularly preferably 0.007 to 0.024% in terms of the concentration when three components, i.e., a concentration calibration-standard substance, an anti-analyte antibody, and antigen-immobilized latex particles, coexist in a reaction system (final concentration in the reaction system).

The nonspecific reaction-avoidance compound of the present invention can be mixed and used with buffer solutions, proteins, salts, preservatives, etc., commonly used in LTIA to the extent that the effect of the present invention is not affected and that the performance as a formulation can be secured.

(Buffer Solutions)
The buffer solutions, for example, are preferably buffer solutions having a buffering action at near neutral pH, preferably pH 6.5 to 7.8, more preferably pH 6.8 to 7.5 (a phosphate buffer solution, a Good's buffer solution, a glycine buffer solution, a borate buffer solution, and a universal buffer solution acquired by combining multiple buffer solutions). A concentration of a buffering agent in these buffer solutions is preferably 0.1 mM to 1 M, more preferably 1 mM to 800 mM, and particularly preferably 5 mM to 500 mM.

From the viewpoint of securing the performance as a formulation, for example, if the antigen is teicoplanin as in Examples described later, a buffering agent having an amine structure in a molecule (e.g., Tris) is not preferred because of an undesirable effect on the preservation stability of teicoplanin. The components other than the nonspecific reaction-avoidance compound of the present invention can be selected by an experiment etc., in consideration of characteristics of each analyte.

(Proteins)
The proteins may include, but not limited to, bovine serum albumin (BSA) and casein. These proteins are used for the purpose of improving preservation stability of antibody- or antigen-immobilized latex particles, or for the purpose of approximating the concentration of protein components introduced into the reaction system from a blood sample and making the reaction environment uniform.

(Salts)
The salts may include, but not limited to, sodium chloride and potassium chloride.

(Preservatives)
The Preservatives may include, but not limited to, antimicrobial agents such as ofloxacin, and sodium azide.

(Assay)
An assay of agglutination inhibition LTIA using the nonspecific reaction-avoidance compound of the present invention can be implemented by using a latex competition method in which the degree of agglutination of antigen-immobilized latex particles is reduced depending on the concentration of the analyte in the test sample, and the analyte can be measured by optically or electrochemically observing the level of resultant agglutination. The method of optical observation may be a method of measuring scattered light intensity, absorbance, or transmitted light intensity with optical equipment.

(Test Sample/Analyte)

A test sample to be measured by the latex agglutination inhibition assay using the nonspecific reaction-avoidance compound of the present invention is blood samples such as serum and plasma. The analyte (detection object) in the test sample may be a low-molecular antigen such as a peptide antigen and hapten, and peptide-based antibiotics such as teicoplanin, arbekacin, and vancomycin, synthetic antibacterial agents such as ofloxacin, and allergens derived from egg white and beans are preferred analytes for a competitive immunoassay. Among these substances, teicoplanin is preferred.

(Antibody)

An antibody used in the present invention may be a polyclonal antibody or a monoclonal antibody. The antibody of the present invention can be a whole antibody molecule or a functional fragment of an antibody having antigen-antibody reaction activity and may be an antibody acquired through immunological operations to common animal (such as a mouse, goat, and sheep) or an antibody acquired by using gene recombination techniques as well as a chimeric antibody. Functional fragments of antibodies include, for example, $F(ab')_2$ and Fab', which are fragments having antigen-antibody reaction activity. These functional fragments of antibodies can be produced by treating antibodies acquired as described above with proteolytic enzymes (e.g., pepsine and papain). These antibodies may or may not be immobilized to latex particles.

(Latex Particles)

Latex particles used in the present invention may be made of polystyrene, styrene-styrene sulfonate copolymers, methacrylic acid polymers, acrylic acid polymers, acrylonitrile-butadiene-styrene copolymers, vinyl chloride-acrylic ester copolymers, polyvinyl chloride acrylate, etc. The latex particles with an average particle diameter of 0.1 μm to 0.4 μm are appropriately selected in consideration of the concentration of the analyte in the test sample or the detection sensitivity of measurement equipment.

(Antigen-Immobilized Latex Particles)

In antigen-immobilized latex particles used in the present invention, either a physical adsorption (hydrophobic bonding) method or a chemical binding method can appropriately be selected as a method for immobilizing antigens depending on the characteristics of the antigens to be immobilized. In the physical adsorption (hydrophobic bonding) method, antigens can be immobilized by a method in which poly-hapten is formed for adsorption and, in the chemical binding method, antigens can be immobilized by introducing a binding functional group such as maleimide group into the antigens or, if the antigens have sugar, by utilizing the sugar to allow the antigens to bind to a binding functional group on the surface of latex particles.

(Agglutination Inhibition LTIA Reagent)

An agglutination inhibition LTIA reagent containing the nonspecific reaction-avoidance compound of the present invention can be provided in, but not limited to, any one of the following typically used forms.

(1) Concentration calibration-standard substance (sometimes called a calibrator, etc.)

(2) Solution containing an antibody to an analyte (sometimes called an antibody solution, a first reagent solution, etc.)

(3) Solution of antigen-immobilized latex particles (sometimes called a latex reagent solution, a second reagent solution, etc.)

(4) Solution for dissolving or diluting the concentration calibration-standard substance (sometimes called a calibrator diluting solution, etc.)

Among these forms, if the nonspecific reaction-avoidance compound of the present invention is contained in the concentration calibration-standard substance (1), the reagent may be provided directly in a form of solution, or may be solidified by means of freeze dehydration etc., after the nonspecific reaction-avoidance compound of the present invention is contained. The reagent may be provided without containing the nonspecific reaction-avoidance compound of the present invention so that the substance can be reconstituted or diluted by a buffer solution etc. containing the nonspecific reaction-avoidance compound of the present invention when used. The buffer solution etc. containing the nonspecific reaction-avoidance compound of the present invention may be provided under the name of a concentration calibration-standard substance (calibrator) diluting solution, a specimen diluting solution, etc., and corresponds to the form of (4) above.

If the nonspecific reaction-avoidance compound of the present invention is contained in the solution containing an antibody to an analyte (2) or the solution of antigen-immobilized latex particles (3), the reagent can be provided as a solution containing the nonspecific reaction-avoidance compound of the present invention.

It is noted that items (1) to (4) above may be provided independently of each other or may collectively be provided as in the case of a kit etc., as long as items (1) to (4) are used in series when agglutination inhibition LTIA is performed.

EXAMPLES

Comparative Example 1

Comparison Between Calibration Curves in the Cases of Diluting Concentration Calibration-Standard Substance with Buffer Solution Containing No Human Serum Component and with Human Serum Containing No Analyte 1. Reagents (1) Teicoplanin (manufactured by Sigma Aldrich)

(2) Serum acquired from humans without teicoplanin administered (serum of 100 persons were pool, hereinafter referred to as the base serum)

(3) Concentration calibration-standard substance-diluting solution (hereinafter referred to as the standard substance-diluting solution): Five-percent (5%) BSA-PBS (pH 7.2), 0.002% ofloxacin, one PBS tablet (DULBECCO's PBS TABLET (-) (manufactured by DS Pharma Biomedical)), 5 g of BSA (Probumin (trademark) Reagent Grade (k) (manufactured by MILLIPORE)), and 2 mg of ofloxacin were diluted with water to 100 mL by using a volumetric flask to prepare the standard substance-diluting solution.

When 100 mL solution of the PBS tablet is prepared, the following composition is acquired:

800 mg of NaCl, 20 mg of KCl, 115 mg of dibasic sodium phosphate (anhydrous), and potassium dihydrogen phosphate (anhydrous).

(4) Anti-teicoplanin antibody solution (containing 2.8 mg/mL anti-teicoplanin sheep polyclonal antibody and 0.5% BSA, pH 7.0, hereinafter referred to as the antibody solution)

(5) Teicoplanin-sensitized latex reagent solution (pH 7.2, hereinafter referred to as the latex reagent solution).

2. Method

Teicoplanin was diluted with the standard substance-diluting solution at 0, 5, 10, 25, 50, and 100 μg/mL and used as a calibrator. Ten serial dilutions of teicoplanin (0, 11, 22, 33, 44, 55, 66, 77, 88, 99, and 110 μg/mL) were made by using the base serum with teicoplanin added at 110 μg/mL and the base serum without teicoplanin added or the standard substance-diluting solution, and used as a simulated specimen solution 1 or a simulated specimen solution 2, respectively. After combining 2.4 μL of the calibrator, the simulated specimen solution 1, or the simulated specimen solution 2 with 180 μL of the anti-teicoplanin antibody solution, the solutions were mixed at 37° C. for 5 minutes. Subsequently, 60 μL of the latex reagent solution was mixed and the absorbance at 700 nm was measured at 37° C. after 1 minute (absorbance I), after 1 minute 20 seconds (absorbance II), after 3 minutes (absorbance III), and after 3 minutes 20 seconds (absorbance IV). A difference was obtained between [an average value of the absorbance II and the absorbance I] and [an average value of the absorbance IV and the absorbance III] and was defined as an absorbance change amount (hereinafter referred to as dabs).

3. Result

Figure 1:
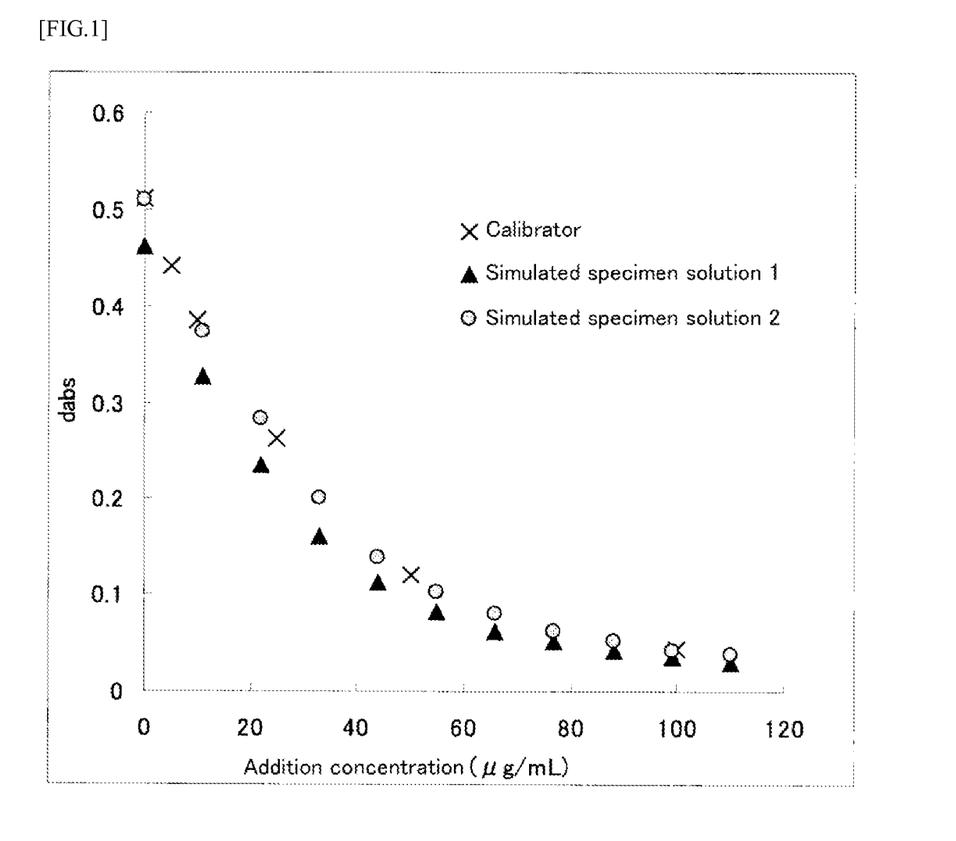
FIG. 1 depicts a calibration curve (×) when a concentration calibration-standard substance is diluted by a buffer solution containing no human serum component, a calibration curve (○) when a human serum with an analyte added is diluted by a buffer solution containing no human serum component, and a calibration curve (▲) when a human serum with an analyte added is diluted by a human serum without the analyte added.

The result is depicted in FIG. 1. The simulated specimen solution 1 (▲) acquired by dilution with the base serum without teicoplanin added indicated that dabs of the base serum itself (teicoplanin concentration, 0 μg/mL) was lower than dabs of the calibrator with a teicoplanin concentration of 0 μg/mL (the standard substance-diluting solution itself) and was lower than dabs of both the calibrator (x) and the simulated specimen solution 2 (○) within the concentration range of 11 to 110 μg/mL and, therefore, nonspecific reactions due to some kind of serum component was suspected.

Example 1

Study for Screening Nonspecific Reaction-Avoidance Compound

1. Reagents (1) Serum acquired from humans without teicoplanin administered (the base serum)

(2) Anti-teicoplanin antibody solution (the antibody solution)

(3) Teicoplanin-sensitized latex reagent solution (the latex reagent solution)

For items (1) to (3) above, the reagents same as those of Comparative Example 1 were used.

(4) 10% BSA-2× PBS (pH 7.0)

One PBS tablet and 5 g of BSA were diluted with water to 50 mL by using a volumetric flask to prepare 10% BSA-2xPBS.

(5) Compounds for screening

The compounds are listed in Table 1.

(a) Blocking N101 and N102 (both manufactured by NOF CORPORATION). Blocking N101 and N102 are blocking reagents for immunological measurement made primarily of synthetic polymers.

(b) Epan 750 (POE-POP block copolymer, manufactured by Dai-ichi Kogyo Seiyaku)

(1) polyoxyethylene content is 50%, polyoxypropylene molecular weight is about 2000

(2) EO number-PO number: (23×2)-34

(c) Pluronic L34 (POE-POP block copolymer, manufactured by ADEKA)

(1) polyoxyethylene content is 40%, polyoxypropylene molecular weight is about 870

(2) EO number-PO number: (7×2)-15

(d) Pluronic F68 (POE-POP block copolymer, manufactured by ADEKA)

(e) Noigen DS601 (POE fatty acid ester, manufactured by Dai-ichi Kogyo Seiyaku)

(f) NIKKOL BC40TX (POE alkyl ether, manufactured by Nikko Chemicals)

(g) NIKKOL BO-10TX (POE alkyl ether, manufactured by Nikko Chemicals)

(h) NIKKOL BT-7 (POE alkyl ether, manufactured by Nikko Chemicals)

(i) NIKKOL BT-9 (POE alkyl ether, manufactured by Nikko Chemicals)

(j) PEG6000 ($H(OCH_2CH_2)_nOH$, average molecular weight: 7300 to 9300, manufactured by Wako Pure Chemical Industries)

(k) Mannitol (manufactured by KISHIDA CHEMICAL)

(l) polybrene (manufactured by Sigma Aldrich)

(m) Heparin sodium (manufactured by Sigma Aldrich)

2. Method

Two point four (2.4) μL of the base serum or 2.4 μL of a test solution 1 (a solution acquired by mixing 10% BSA-2× PBS with the compound for screening prepared at two-fold concentration of the final concentration described in Table 1 at a volume ratio of 1:1) was combined with 180 μL of the antibody solution and mixed at 37° C. for 5 minutes. Subsequently, 60 μL of the latex reagent solution was mixed and the absorbance at 700 nm was measured at 37° C. after 1 minute (absorbance I), after 1 minute 20 seconds (absorbance II), after 3 minutes (absorbance III), and after 3 minutes 20 seconds (absorbance IV). A difference was obtained between [an average value of the absorbance II and the absorbance I] and [an average value of the absorbance IV and the absorbance III] and was defined as dabs. It was determined that the compound was effective when a negative difference was acquired from following Formula (A):

(dabs of the base serum)−(dabs of a test solution 1)  Formula (A).

A solution acquired by adding purified water instead of the nonspecific reaction-avoidance compound was used as a control.

3. Result

Pluronic F68, Noigen DS601, NIKKOL BC40TX, NIKKOL BO-10TX, NIKKOL BT-7, and NIKKOL BT-9 were determined as being effective and defined as nonspecific reaction-avoidance compounds. Epan 750 and polybrene were also defined as nonspecific reaction-avoidance compound candidates because of the difference from the base serum.

TABLE 1

| Type | Final concentration | dabs | Difference from serum |
|---|---|---|---|
| Serum |  | 0.4788 | 0.0000 |
| Control |  | 0.5129 | 0.0341 |
| Blocking N101 | ½ | 0.5068 | 0.0280 |
| Blocking N102 | ½ | 0.5257 | 0.0469 |
| Epan 750 | 5% | 0.4872 | 0.0084 |
| Pluronic L34 | 5% | 0.5114 | 0.0326 |
| Pluronic F68 | 5% | 0.4371 | −0.0417 |
| Noigen DS601 | 0.5% | 0.4430 | −0.0358 |
| NIKKOL BC40TX | 5% | 0.3476 | −0.1312 |
| NIKKOL BO-10TX | 5% | 0.4296 | −0.0492 |

TABLE 1-continued

| Type | Final concentration | dabs | Difference from serum |
|---|---|---|---|
| NIKKOL BT-7 | 5% | 0.4070 | −0.0718 |
| NIKKOL BT-9 | 5% | 0.4245 | −0.0543 |
| PEG6000 | 5% | 0.5441 | 0.0653 |
| Mannitol | 5% | 0.5088 | 0.0300 |
| Polybrene | 5 mg/mL | 0.4989 | 0.0201 |
| Heparin | 5 mg/mL | 0.5100 | 0.0312 |

Note:
Among final concentrations described in Table 1, "1/2" indicates a degree of dilution (two-fold dilution) when undiluted solutions of commercialized products are defined as 1.

Example 2

Study of Effective Concentration Range of Nonspecific Reaction-Avoidance Compound (Candidate)-1

The nonspecific reaction-avoidance compound candidates narrowed down from the result of Example 1 were studied in terms of effective concentration ranges.

1. Reagents
(1) Serum acquired from humans without teicoplanin administered (the base serum)
(2) Anti-teicoplanin antibody solution (the antibody solution)
(3) Teicoplanin-sensitized latex reagent solution (the latex reagent solution)
For items (1) to (3) above, the reagents same as those of Comparative Example 1 were used.
(4) 10% BSA-2× PBS (pH 7.0)
(5) Nonspecific reaction-avoidance compound (candidate)

The compounds are listed in Table 2.
(a) Epan 485 (POE-POP block copolymer, manufactured by Dai-ichi Kogyo Seiyaku)
(b) Pluronic F68
(c) Pluronic F88
(d) Noigen DS601
(e) NIKKOL BT-7
(f) NIKKOL BT-9
(g) Polybrene 2. Method Two point four (2.4) μL of the base serum or 2.4 μL of a test solution 2 (a solution acquired by mixing 10% BSA-2xPBS with the additive compound prepared at two-fold concentration of the final concentration described in Table 2 at a ratio of 1:1) was combined with 180 μL of the antibody solution and mixed at 37° C. for 5 minutes. Subsequently, 60 μL of the latex reagent solution was mixed and the absorbance at 700 nm was measured at 37° C. after 1 minute (absorbance I), after 1 minute 20 seconds (absorbance II), after 3 minutes (absorbance III), and after 3 minutes 20 seconds (absorbance IV). A difference was obtained between [an average value of the absorbance II and the absorbance I] and [an average value of the absorbance IV and the absorbance III] and was defined as dabs. It was determined that the compound was effective when a ratio of 95% to 105% was acquired from following Formula (B):

(dabs of the base serum)/(dabs of a test solution 2)     Formula (B).

3. Result

Pluronic F68, Pluronic F88, Noigen DS601, NIKKOL BT-7, NIKKOL BT-9, and polybrene were determined as being effective. It was presumed that Epan 485 is also effective when the final concentration is increased. From above, these compounds are determined as nonspecific reaction-avoidance compounds.

TABLE 2

| Type | Final conc. | dabs | | | (Ratio to serum) | | |
|---|---|---|---|---|---|---|---|
| | | Exp. 1 | Exp. 2 | Exp. 3 | Exp. 1 | Exp. 2 | Exp. 3 |
| Serum | | 0.4783 | 0.4829 | 0.4812 | 100.0% | 100.0% | 100.0% |
| Control | | 0.5125 | 0.5169 | 0.5226 | 107.2% | 107.0% | 108.6% |
| Epan 485 | 2.5% | 0.5052 | | | 105.6% | | |
| | 0.5% | 0.5115 | | | 106.9% | | |
| | 0.1% | 0.5138 | | | 107.4% | | |
| Pluronic F68 | 2.5% | 0.4571 | | | 95.6% | | |
| | 0.5% | 0.4974 | | | 104.0% | | |
| | 0.1% | 0.5094 | | | 106.5% | | |
| Pluronic F88 | 2.5% | 0.4558 | 0.4593 | 0.4610 | 95.3% | 95.1% | 95.8% |
| | 0.5% | 0.4992 | 0.4993 | 0.4997 | 104.4% | 103.4% | 103.8% |
| | 0.1% | 0.5111 | 0.5127 | 0.5127 | 106.9% | 106.2% | 106.5% |
| Noigen DS601 | 0.25% | 0.4532 | | | 94.8% | | |
| | 0.05% | 0.4960 | | | 103.7% | | |
| | 0.01% | 0.5049 | | | 105.6% | | |
| NIKKOL BT-7 | 2.5% | 0.4700 | 0.4698 | | 98.3% | 97.3% | |
| | 0.5% | 0.5104 | 0.5083 | | 106.7% | 105.3% | |
| | 0.1% | 0.5178 | 0.5111 | | 108.3% | 105.8% | |
| NIKKOL BT-9 | 2.5% | 0.4732 | 0.4727 | 0.4757 | 98.9% | 97.9% | 98.9% |
| | 0.5% | 0.5112 | 0.5081 | 0.5083 | 106.9% | 105.2% | 105.6% |
| | 0.1% | 0.5126 | 0.5049 | 0.5035 | 107.2% | 104.6% | 104.6% |
| Polybrene | 50 mg/mL | 0.3777 | 0.3777 | | 79.0% | | |
| | 25 mg/mL | 0.4859 | 0.4871 | | 101.6% | | |
| | 10 mg/mL | 0.5017 | 0.5090 | | 104.9% | | |

Note:
A blank indicates that the test was not conducted.

Example 3

Study of Concentration Range of Nonspecific Reaction-Avoidance Compound-2

1. Reagents
(1) Serum acquired from humans without teicoplanin administered (the base serum)
(2) Anti-teicoplanin antibody solution (the antibody solution)
(3) Teicoplanin-sensitized latex reagent solution (the latex reagent solution)
For items (1) to (3) above, the reagents same as those of Comparative Examples 1 and 2 were used.
(4) 10% BSA-2× PBS (pH 7.0)
(5) Nonspecific reaction-avoidance compounds
(a) Pluronic F88
(b) NIKKOL BT-9

2. Method

Two point four (2.4) μL of the base serum as well as a test solution 3 (a solution acquired by mixing 10% BSA-2xPBS with the additive compound prepared at two-fold concentration of the final concentration described in Table 3 at a ratio of 1:1) was combined with 180 μL of the antibody solution and mixed at 37° C. for 5 minutes. Subsequently, 60 μL of the latex reagent solution was mixed and the absorbance at 700 nm was measured at 37° C. after 1 minute (absorbance I), after 1 minute 20 seconds (absorbance II), after 3 minutes (absorbance III), and after 3 minutes 20 seconds (absorbance IV). A difference was obtained between [an average value of the absorbance II and the absorbance I] and [an average value of the absorbance IV and the absorbance III] and was defined as dabs.

The concentration resulting in a smallest ratio from following Formula (C) was calculated by single regression analysis.

(dabs of the base serum)/(dabs of a test solution 3)  Formula (C).

3. Result

Pluronic F88 yielded the smallest difference from the base serum at 1.75%. NIKKOL BT-9 yielded the smallest difference from the base serum at 2.5%.

For items (1) to (3) above, the reagents same as those of Comparative Examples 1 and 2 were used.
(4) Nonspecific reaction-avoidance compound
Pluronic F88

2. Method

The following six types of test solution 4 were prepared.
BSA 0%, PB−
The solution was acquired by weighing and diluting 1.75 g of sodium chloride, 0.7 g of Pluronic F88, and 2 mg of ofloxacin to 100 mL by using a volumetric flask.
BSA 5%, PB−
The solution was acquired by weighing and diluting 1.75 g of sodium chloride, 0.7 g of Pluronic F88, 5 g of BSA, and 2 mg of ofloxacin to 100 mL by using a volumetric flask.
BSA 10%, PB−
The solution was acquired by weighing and diluting 1.75 g of sodium chloride, 0.7 g of Pluronic F88, 10 g of BSA, and 2 mg of ofloxacin to 100 mL by using a volumetric flask.
BSA 0%, PB+
The solution was acquired by weighing and diluting one PBS tablet, 0.7 g of Pluronic F88, and 2 mg of ofloxacin to 100 mL by using a volumetric flask.
BSA 5%, PB+
The solution was acquired by weighing and diluting one PBS tablet, 0.7 g of Pluronic F88, 5 g of BSA, and 2 mg of ofloxacin to 100 mL by using a volumetric flask.
BSA 10%, PB+
The solution was acquired by weighing and diluting one PBS tablet, 0.7 g of Pluronic F88, 10 g of BSA, and 2 mg of ofloxacin to 100 mL by using a volumetric flask.

Two point four (2.4) μL of the base serum as well as a test solution 4 of said six types was combined with 180 μL of the antibody solution and mixed at 37° C. for 5 minutes. Subsequently, 60 μL of the latex reagent solution was mixed and the absorbance at 700 nm (absorbance I-IV) was measured at 37° C. after 1 minute (absorbance I), after 1 minute 20 seconds (absorbance II), after 3 minutes (absorbance III), and after 3 minutes 20 seconds (absorbance IV). A difference was obtained between [an average value of the absorbance II and the absorbance I] and [an average value of the absorbance IV and the absorbance III] and was defined as

TABLE 3

| Type | Final conc. | dabs Exp. 1 | dabs Exp. 2 | dabs Exp. 3 | (Ratio to serum) Exp. 1 | (Ratio to serum) Exp. 2 | (Ratio to serum) Exp. 3 |
|---|---|---|---|---|---|---|---|
| Serum |  | 0.4880 | 0.4904 | 0.4835 | 100.0% | 100.0% | 100.0% |
| Pluronic F88 | 2.00% | 0.4799 | 0.4801 | 0.4825 | 98.3% | 97.9% | 99.8% |
|  | 1.75% | 0.4845 | 0.4830 | 0.4857 | 99.3% | 98.5% | 100.5% |
|  | 1.50% | 0.4912 | 0.4861 | 0.4966 | 100.7% | 99.1% | 102.7% |
| NIKKOL BT-9 | 2.50% | 0.4817 | 0.4879 | 0.4855 | 98.7% | 99.5% | 100.4% |
|  | 2.25% | 0.4872 | 0.4929 | 0.4930 | 99.8% | 100.5% | 102.0% |
|  | 2.00% | 0.4919 | 0.4940 | 0.4932 | 100.8% | 100.7% | 102.0% |

Reference Example 1

Study of Buffer Composition

1. Reagents
(1) Serum acquired from humans without teicoplanin administered (the base serum)
(2) Anti-teicoplanin antibody solution (the antibody solution)
(3) Teicoplanin-sensitized latex reagent solution (the latex reagent solution)

dabs. A ratio was calculated by following Formula (D) to confirm the effect of the buffer composition:

(dabs of the base serum)−(dabs of a test solution 4)  Formula (D).

3. Result

Figure 2:
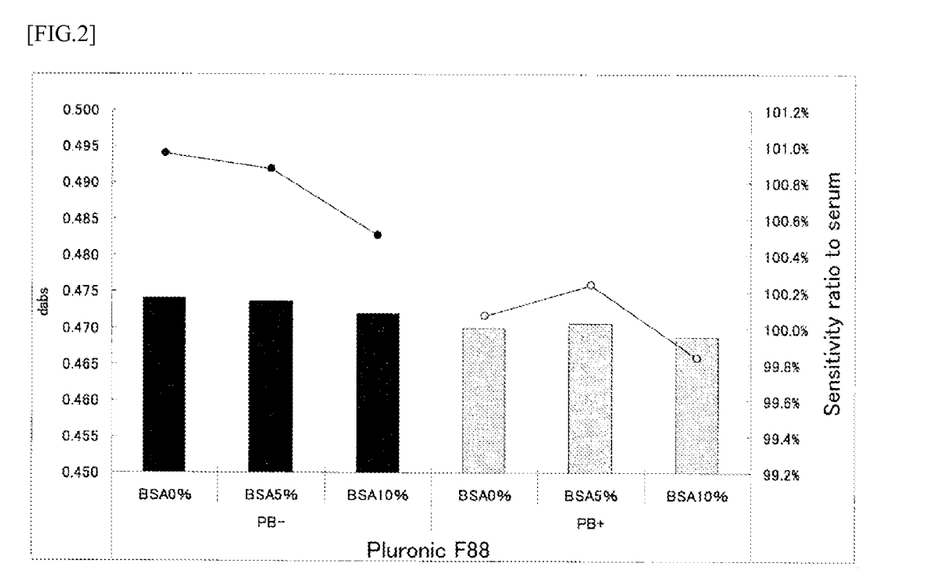
FIG. 2 is a diagram of the result of study on the composition of a concentration calibration-standard substance-diluting solution containing a nonspecific reaction-avoidance compound of the present invention.

The result is shown in FIG. 2. It was confirmed that PBS improves the effect of the nonspecific reaction-avoidance compound of the present invention. On the other hand, BSA did not affect the effect of the nonspecific reaction-avoidance compound.

As described above, from the results of Comparative Example 1, Examples 1 to 3, and Reference Example 1, it was confirmed that the POE-POP block copolymers, the POE alkyl ethers, the POE fatty acid esters, and the polyvalent quaternary amine polymer compounds enable the avoidance of nonspecific reactions resulting in the absence of agglutination that should occur in agglutination inhibition LTIA.

The nonspecific reaction-avoidance compound of the present invention was confirmed to have unconventional characteristics that the addition to a concentration calibration-standard substance (calibrator) allows the compound to exert the effect thereof.

Example 4

Comparison between Calibration Curves in the Cases of Diluting Concentration Calibration-Standard Substance with Buffer Solution Containing Nonspecific Reaction-Avoidance Compound of Present Invention and with Human Serum Containing No Analyte 1. Reagents
(1) Teicoplanin (manufactured by Sigma Aldrich)
(2) Serum acquired from humans without teicoplanin administered (hereinafter referred to as the base serum)
(3) Concentration calibration-standard substance-diluting solution (hereinafter referred to as the standard substance-diluting solution): 5% BSA-PBS (pH 7.2), 0.002% ofloxacin, 0.7% Pluronic F88
(4) Anti-teicoplanin antibody solution (the antibody solution)
(5) Teicoplanin-sensitized latex reagent solution (the latex reagent solution)

2. Method
Teicoplanin was diluted with the standard substance-diluting solution at 0, 5, 10, 25, 50, and 100 μg/mL and used as a calibrator. Ten serial dilutions of teicoplanin (0, 10, 20, 30, 40, 50, 60, 70, 80, 90, and 100 μg/mL) were made by using the base serum with teicoplanin added at 110 μg/mL and the base serum without teicoplanin added, and used as a simulated specimen solution 3. Two point four (2.4) μL of the calibrator or the simulated specimen solution 3 was combined with 180 μL of the anti-teicoplanin antibody solution and mixed at 37° C. for 5 minutes. Subsequently, 60 μL of the latex reagent solution was mixed and the absorbance at 700 nm was measured at 37° C. after 1 minute (absorbance I), after 1 minute 20 seconds (absorbance II), after 3 minutes (absorbance III), and after 3 minutes 20 seconds (absorbance IV). A difference was obtained between [an average value of the absorbance II and the absorbance I] and [an average value of the absorbance IV and the absorbance III] and was defined as dabs.

Figure 3:
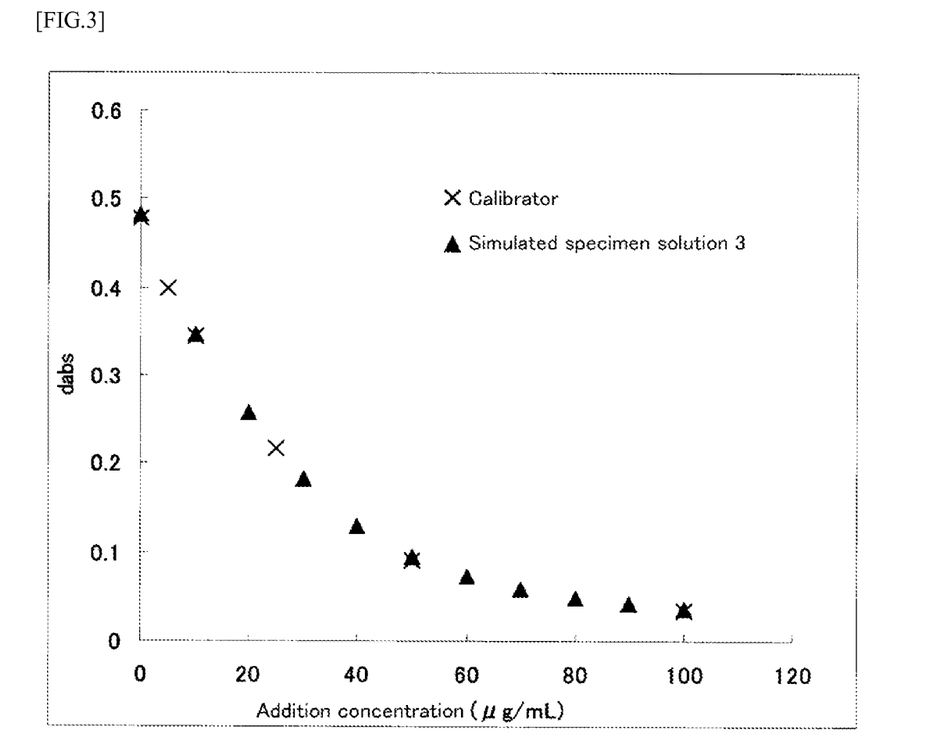
FIG. 3 depicts a calibration curve (×) when the concentration calibration-standard substance is diluted by the concentration calibration-standard substance-diluting solution of the present invention, and a calibration curve (▲) when a human serum with an analyte added is diluted by a human serum without the analyte added.

3. Result
The result is shown in FIG. 3. The simulated specimen solution 3 (▲) acquired by dilution with the base serum without teicoplanin added and the calibrator (×) were identical in terms of dabs at all the teicoplanin concentrations in the concentration range of 0 to 110 μg/mL. From above, the effect of the present invention was confirmed.

INDUSTRIAL APPLICABILITY

The present invention provides a method capable of avoiding nonspecific reactions resulting in the absence of agglutination that should occur in agglutination inhibition LTIA. The present invention enables accurate measurement of an analyte in a blood sample by agglutination inhibition LTIA.

The invention claimed is:
1. A method of avoiding nonspecific reactions in a latex agglutination inhibition test, comprising performing a latex agglutination inhibition assay, wherein the assay is performed by using the following items (1) to (3), wherein one or more compounds selected from the group consisting of polyoxyethylene-polyoxypropylene block copolymers, polyoxyethylene alkyl ethers, polyoxyethylene fatty acid esters, and polyvalent quaternary amine polymer compounds are contained in following item (1):
(1) a plurality of solutions containing serial concentrations of a concentration calibration-standard substance, wherein said plurality of solutions consist of water, said concentration calibration-standard substance, said one or more compounds, a buffering agent, a protein, and optionally, a salt, and/or a preservative, wherein said salt is sodium chloride and/or potassium chloride, and wherein said preservative is antimicrobial agent and/or sodium azide,
(2) a solution containing an anti-analyte antibody, wherein the solution (2) does not comprise an analyte to the anti-analyte antibody, and
(3) a solution containing antigen-immobilized latex particles, wherein the solution (3) does not comprise an analyte that is the antigen,
wherein the polyoxyethylene-polyoxypropylene block copolymers are represented by Formula (I):

$$HO(C_2H_4O)_a—(C_3H_6O)_b—(C_2H_4O)_cH \quad (I)$$

wherein a, b, and c denote arbitrary integers and a+c is determined so as to represent an ethylene oxide with an average degree of polymerization of 4 to 200 units while b is determined so as to represent a propylene oxide with an average degree of polymerization of 5 to 100 units;
wherein the polyoxyethylene alkyl ethers are represented by Formula (II):

$$R^1O(C_2H_4O)_nH \quad (II)$$

wherein $R^1$ denotes an alkyl group having a carbon number of 8 to 20, wherein the alkyl group is either primary or secondary and optionally has double bond(s) in the alkyl group, and n denotes an arbitrary integer from 7 to 40;
wherein the polyoxyethylene fatty acid esters are represented by Formula (III):

$$R^2COO(C_2H_4O)_nR^3 \quad (III)$$

wherein $R^2$ denotes an alkyl group having a carbon number of 16 to 18, wherein the alkyl group optionally has double bond(s), and n denotes an arbitrary integer from 170 to 180 while $R^3$ denotes a hydrogen atom or an $R^2COO$ group; and
wherein the polyvalent quaternary amine polymer compounds are hexadimethrine bromide.

2. The method of claim 1, wherein the one or more compounds comprises polyoxyethylene-polyoxypropylene block copolymers represented by Formula (I):

$$HO(C_2H_4O)_a—(C_3H_6O)_b—(C_2H_4O)_cH \quad (I)$$

wherein a, b, and c denote arbitrary integers and a+c is determined so as to represent an ethylene oxide with an average degree of polymerization of 4 to 200 units while b is determined so as to represent a propylene oxide with an average degree of polymerization of 5 to 100 units.

3. The method of claim 1, wherein the one or more compounds comprises polyoxyethylene alkyl ethers represented by Formula (II):

$$R^1O(C_2H_4O)_nH \quad (II)$$

wherein $R^1$ denotes an alkyl group having a carbon number of 8 to 20, wherein the alkyl group may be either primary or secondary and may have a double bond(s) in the alkyl group, and n denotes an arbitrary integer from 7 to 40.

4. The method of claim 1, wherein the one or more compounds comprises polyoxyethylene fatty acid esters represented by Formula (III):

$$R^2COO(C_2H_4O)_nR^3 \quad (III)$$

wherein $R^2$ denotes an alkyl group having a carbon number of 16 to 18, wherein the alkyl group may have a double bond(s), and n denotes an arbitrary integer from 170 to 180 while $R^3$ denotes a hydrogen atom or an $R^2COO$ group.

5. The method of claim 1, wherein the one or more compounds comprises hexadimethrine bromide.

6. A reagent for a latex agglutination inhibition assay, wherein one or more compounds selected from the group consisting of polyoxyethylene-polyoxypropylene block copolymers, polyoxyethylene alkyl ethers, polyoxyethylene fatty acid esters, and polyvalent quaternary amine polymer compounds are contained in following item (1):

(1) a plurality of solutions containing serial concentrations of a concentration calibration-standard substance, wherein said plurality of solutions consist of water, said concentration calibration-standard substance, said one or more compounds, a buffering agent, a protein, and optionally, a salt, and/or a preservative, wherein said salt is sodium chloride and/or potassium chloride, and wherein said preservative is antimicrobial agent and/or sodium azide, wherein the polyoxyethylene-polyoxypropylene block copolymers are represented by Formula (I):

$$HO(C_2H_4O)_a-(C_3H_6O)_b-(C_2H_4O)_cH \quad (I)$$

wherein a, b, and c denote arbitrary integers and a+c is determined so as to represent an ethylene oxide with an average degree of polymerization of 4 to 200 units while b is determined so as to represent a propylene oxide with an average degree of polymerization of 5 to 100 units, wherein the polyoxyethylene alkyl ethers are represented by Formula (II):

$$R^1O(C_2H_4O)_nH \quad (II)$$

wherein $R^1$ denotes an alkyl group having a carbon number of 8 to 20, wherein the alkyl group is either primary or secondary and optionally has double bond(s) in the alkyl group, and n denotes an arbitrary integer from 7 to 40, wherein the polyoxyethylene fatty acid esters are represented by Formula (III):

$$R^2COO(C_2H_4O)_nR^3 \quad (III)$$

wherein $R^2$ denotes an alkyl group having a carbon number of 16 to 18, wherein the alkyl group optionally has double bond(s), and n denotes an arbitrary integer from 170 to 180 while $R^3$ denotes a hydrogen atom or an $R^2COO$ group, and wherein the polyvalent quaternary amine polymer compounds are hexadimethrine bromide.

7. The reagent of claim 6, wherein the concentration calibration-standard substance is teicoplanin.

8. The reagent of claim 6 or 7, wherein the one or more compounds comprises polyoxyethylene-polyoxypropylene block copolymers represented by Formula (I):

$$HO(C_2H_4O)_a-(C_3H_6O)_b-(C_2H_4O)_cH \quad (I)$$

wherein a, b, and c denote arbitrary integers and a+c is determined so as to represent an ethylene oxide with an average degree of polymerization of 4 to 200 units while b is determined so as to represent a propylene oxide with an average degree of polymerization of 5 to 100 units.

9. The reagent of claim 6 or 7, wherein the one or more compounds comprises polyoxyethylene alkyl ethers represented by Formula (II):

$$R^1O(C_2H_4O)_nH \quad (II)$$

wherein $R^1$ denotes an alkyl group having a carbon number of 8 to 20, wherein the alkyl group is either primary or secondary and optionally has double bond(s) in the alkyl group, and n denotes an arbitrary integer from 7 to 40.

10. The reagent of claim 6 or 7, wherein the one or more compounds comprises polyoxyethylene fatty acid esters represented by Formula (III):

$$R^2COO(C_2H_4O)_nR^3 \quad (III)$$

wherein $R^2$ denotes an alkyl group having a carbon number of 16 to 18, wherein the alkyl group optionally has double bond(s), and n denotes an arbitrary integer from 170 to 180 while $R^3$ denotes a hydrogen atom or an $R^2COO$ group.

11. The reagent of claim 6 or 7, wherein the one or more compounds comprises hexadimethrine bromide.

12. A kit of reagents for a latex agglutination inhibition assay, comprising the following solutions (1) to (3), wherein one or more compounds selected from the group consisting of polyoxyethylene-polyoxypropylene block copolymers, polyoxyethylene alkyl ethers, polyoxyethylene fatty acid esters, and polyvalent quaternary amine polymer compounds are contained in following item (1):

(1) a plurality of solutions containing serial concentrations of a concentration calibration-standard substance, wherein said plurality of solutions consist of water, said concentration calibration-standard substance, said one or more compounds, a buffering agent a protein, and optionally, a salt, and/or a preservative, wherein said salt is sodium chloride and/or potassium chloride, and wherein said preservative is antimicrobial agent and/or sodium azide, (2) a solution containing an anti-analyte antibody, wherein the solution (2) does not comprise an analyte to the anti-analyte antibody, and (3) a solution containing antigen-immobilized latex particles, wherein the solution (3) does not comprise an analyte that is the antigen, wherein the polyoxyethylene-polyoxypropylene block copolymers are represented by Formula (I):

$$HO(C_2H_4O)_a-(C_3H_6O)_b-(C_2H_4O)_cH \quad (I)$$

wherein a, b, and c denote arbitrary integers and a+c is determined so as to represent an ethylene oxide with an average degree of polymerization of 4 to 200 units while b is determined so as to represent a propylene oxide with an average degree of polymerization of 5 to 100 units, wherein the polyoxyethylene alkyl ethers are represented by Formula (II):

$$R^1O(C_2H_4O)_nH \quad (II)$$

wherein $R^1$ denotes an alkyl group having a carbon number of 8 to 20, wherein the alkyl group is either primary or secondary and optionally has double bond(s) in the alkyl group, and n denotes an arbitrary integer from 7 to 40, wherein the polyoxyethylene fatty acid esters are represented by Formula (III):

$$R^2COO(C_2H_4O)_nR^3 \quad (III)$$

wherein $R^2$ denotes an alkyl group having a carbon number of 16 to 18, wherein the alkyl group optionally has double bond(s), and n denotes an arbitrary integer from 170 to 180 while $R^3$ denotes a hydrogen atom or an $R^2COO$ group, and wherein the polyvalent quaternary amine polymer compounds are hexadimethrine bromide.

13. The method of claim 1, wherein the concentration calibration-standard substance is peptide-based antibiotics or synthetic antibacterial agents, the solution containing an anti-analyte antibody is a solution containing an anti-peptide-based antibiotic antibody or an anti-synthetic antibacterial agent antibody, and the solution containing antigen-immobilized latex particles is a solution containing peptide-based antibiotic-immobilized latex particles or synthetic antibacterial agent-immobilized latex particles, respectively.

14. The reagent of claim 6, wherein the concentration calibration-standard substance is peptide-based antibiotics or synthetic antibacterial agents.

15. The kit of claim 12, wherein the concentration calibration-standard substance is peptide-based antibiotics or synthetic antibacterial agents, the solution containing an anti-analyte antibody is a solution containing an anti-peptide-based antibiotic antibody or an anti-synthetic antibacterial agent antibody, and the solution containing antigen-immobilized latex particles is a solution containing peptide-based antibiotic-immobilized latex particles or synthetic antibacterial agent-immobilized latex particles, respectively.

* * * * *